(12) United States Patent
Gay et al.

(10) Patent No.: US 9,924,920 B2
(45) Date of Patent: Mar. 27, 2018

(54) PHANTOM INTENDED FOR USE IN QUALITY CONTROL OF TOMOGRAPHIC IMAGES

(71) Applicants: SAFRAN, Paris (FR); SAFRAN LANDING SYSTEMS, Velizy-Villacoublay (FR); SAFRAN AIRCRAFT ENGINES, Paris (FR)

(72) Inventors: Lionel Christian Jean-Loïc Gay, Yerres (FR); Philippe Arslan, Alfortville (FR); Yves Rambourg, Gif-sur-yvette (FR); André Chandelle, Moissy-Cramayel (FR)

(73) Assignees: SAFRAN, Paris (FR); SAFRAN LANDING SYSTEMS, Velizy-Villacoublay (FR); SAFRAN AIRCRAFT ENGINES, Paris (FR)

( * ) Notice: Subject to any disclaimer, the term of this patent is extended or adjusted under 35 U.S.C. 154(b) by 0 days.

(21) Appl. No.: 15/538,750

(22) PCT Filed: Dec. 22, 2015

(86) PCT No.: PCT/FR2015/053733
§ 371 (c)(1),
(2) Date: Jun. 22, 2017

(87) PCT Pub. No.: WO2016/102896
PCT Pub. Date: Jun. 30, 2016

(65) Prior Publication Data
US 2017/0370859 A1  Dec. 28, 2017

(30) Foreign Application Priority Data
Dec. 23, 2014  (FR) ...................................... 14 63208

(51) Int. Cl.
*A61B 6/03* (2006.01)
*G01N 23/04* (2006.01)
*A61B 6/00* (2006.01)

(52) U.S. Cl.
CPC ........... *A61B 6/583* (2013.01); *G01N 23/046* (2013.01); *A61B 2560/0228* (2013.01); *G01N 2223/3035* (2013.01); *G01N 2223/645* (2013.01)

(58) Field of Classification Search
CPC ........ G01N 23/00; G01N 23/02; G01N 23/04; G01N 23/046; G01N 23/06; G01N 23/08;
(Continued)

(56) References Cited

U.S. PATENT DOCUMENTS 5,793,835 A * 8/1998 Blanck .................. A61B 6/583
378/18
7,056,019 B1 * 6/2006 Hanson .................. A61B 6/583
378/18
(Continued)

FOREIGN PATENT DOCUMENTS

EP  0 875 751 A1  11/1998
GB  2504258 A * 1/2014 ............. G01T 1/169

OTHER PUBLICATIONS

International Search Report as issued in International Patent Application No. PCT/FR2015/053733, dated Mar. 15, 2016.
(Continued)

*Primary Examiner* — Anastasia Midkiff
(74) *Attorney, Agent, or Firm* — Pillsbury Winthrop Shaw Pittman LLP

(57) ABSTRACT

A phantom for use in quality control of tomographic images, the phantom including a cylindrical plate made of a uniform material having a density d1, with two cylinders being inserted in the plate, the cylinders being made out of uniform
(Continued)

materials having different densities d2, d3, the density of one of the cylinders being greater than the density d1 of the plate, and the density of the other cylinder being less than the density d1 of the plate, and including a first series of pairs of holes of different diameters drilled in the plate, the axes of the holes of the first series being oriented axially relative to an axis of revolution of the plate, and the holes in a given pair being spaced apart from each other by a distance equal to their diameter.

10 Claims, 2 Drawing Sheets

(58) Field of Classification Search
CPC .. G01N 23/083; G01N 23/10; G01N 2223/00; G01N 2223/03; G01N 2223/04; G01N 2223/30; G01N 2223/303; G01N 2223/3035; G01N 2223/40; G01N 2223/419; G01N 2223/60; G01N 2223/639; G01N 2223/64; G01N 2223/645; A61B 6/00; A61B 6/02; A61B 6/03; A61B 6/032; A61B 6/035; A61B 6/58; A61B 6/582; A61B 6/583; A61B 2560/00; A61B 2560/02; A61B 2560/0223; A61B 2560/0228; A61B 2560/0233

See application file for complete search history.

(56) References Cited

U.S. PATENT DOCUMENTS

| | | | |
|---|---|---|---|
| 2009/0190723 A1* | 7/2009 | Jang | A61B 6/5276 378/207 |
| 2012/0128132 A1* | 5/2012 | Coolens | A61B 6/583 378/207 |

OTHER PUBLICATIONS

Hanson, K. >., et al., "Computed tomography using proton energy loss," Physics in Medicine and Biology, Institute of Physics Publishing, vol. 26, No. 6, Nov. 1981, ISSN: 0031-9155, pp. 965-983.
International Preliminary Report on Patentability and the Written Opinion of the International Searching Authority as issued in International Patent Application No. PCT/FR2015/053733, dated Jun. 27, 2017.

* cited by examiner

PHANTOM INTENDED FOR USE IN QUALITY CONTROL OF TOMOGRAPHIC IMAGES

CROSS REFERENCE TO RELATED APPLICATIONS

This application is the U.S. National Stage of PCT/FR2015/053733 filed Dec. 22, 2015, which in turn claims priority to French Application No. 1463208, filed Dec. 23, 2014. The contents of both applications are incorporated herein by reference in their entirety.

BACKGROUND OF THE INVENTION

The present invention relates to the general field of quality control in two-dimensional (2D) or three-dimensional (3D) tomographic imaging.

A preferred, but nonexclusive, application lies in quality control for tomographic images of parts made out of composite material and used in particular in the field of aviation.

Tomography is a technique commonly in use in the field of nondestructive quality control of parts in order to obtain a 2D or 3D reconstruction of internal defects of a part. By using an imaging appliance, this technique makes it possible to view and to quantify accurately the characteristics of defects inside a part (three-dimensional position, size, form factor, etc.).

Furthermore, it is known to use image quality indicators (IQI) for evaluating the quality of tomographic images acquired using the imaging appliance. Typically, such IQIs are phantoms (which may also be called calibration parts) that include inclusions and asperities acting as defects. In association with a computer program, such phantoms thus assist in determining one or more parameters characterizing the quality of tomographic images, such as in particular spatial resolution in various directions, signal-to-noise ratio, uniformity, etc.

Nevertheless, presently-known phantoms are not adapted to the quality control of parts, and in particular of parts made out of composite material. In particular, such phantoms are generally prismatic in shape, giving rise to artifacts in the tomographic data obtained from the 2D or 3D reconstruction of the part.

There thus exists a need to be able to have a phantom for quality control in 2D or 3D imaging of parts, but without presenting the above-mentioned drawbacks.

OBJECT AND SUMMARY OF THE INVENTION

The present invention satisfies this need in particular by proposing a phantom designed to be used for quality control of tomographic images, the phantom comprising:
- a cylindrical plate made of a uniform material having density d1, said cylindrical plate presenting an axis of revolution;
- two cylinders inserted in the plate, the cylinders being made of uniform material having different densities d2, d3, the density of one of the cylinders being greater than the density d1 of the plate, and the density of the other cylinder being less than the density d1 of the plate; and
- a first series of pairs of holes of different diameters drilled in the plate, the holes of the first series extending along axes that are parallel to the axis of revolution of the plate, the phantom being characterized in that it further comprises a second series of pairs of holes of different diameters drilled in the plate, the holes of the second series extending along axes perpendicular to the axis of revolution of the plate so that said holes of the second series extend radially in the cylindrical plate.

The phantom of the invention is well adapted to quality control of 2D or 3D tomographic images, in particular on parts made of composite material, without disturbing the quality of the image of the part being inspected. The cylindrical shape of the plate of the phantom make it possible to reduce tomographic artifacts that might be generated by the phantom itself. Furthermore, the phantom of the invention presents three different densities, thus making it possible to establish a calibration curve for accurately measuring the density of the part being inspected.

The holes drilled in the plate of the phantom of the invention make it possible to measure the resolution of the tomography. The presence of holes presents the advantage of making it possible to perform such a measurement without having recourse to high-density metal wires that would, in particular, radiate relative to the material of the part being inspected.

In an application to quality control of 3D tomographic images, the holes in a given pair of holes in the first series and in the second series of pairs of holes are spaced apart from each other by a distance equal to their diameter.

In this application, the holes of the first series are preferably of diameters that are identical to the holes of the second series. Furthermore, the holes of the second series may open out into a peripheral edge of the plate at the same height of said peripheral edge. Under such circumstances, the holes of the second series are advantageously angularly distributed around the axis of revolution of the plate.

As for the holes of the first series, they may open out into both opposite faces of the plate, the pairs of holes being arranged on different diameters of the plate. Under such circumstances, the pairs of holes of the first series are advantageously arranged in order of decreasing diameter between the outer periphery of the plate and the center of said plate.

The plate of the phantom may be made out of a uniform material presenting relative density d1 lying in the range 1.2 to 8 close to the density of the part being inspected.

The two cylinders of the phantom inserted in the plate have respective axes of revolution that may be positioned on a common diameter of the plate.

The invention also provides the use of at least one phantom as defined above for quality control in tomographic imaging of a gas turbine engine fan blade made out of composite material, wherein the plate presents a diameter of about 50 mm and a thickness of about 6 mm, each of the two cylinders has a diameter of about 10 mm, and the holes of the first series of holes have diameters lying in the range 0.2 mm to 1.2 mm, approximately.

BRIEF DESCRIPTION OF THE DRAWINGS

Other characteristics and advantages of the present invention appear from the following description made with reference to the accompanying drawings, which show an implementation having no limiting character. In the figures.

DETAILED DESCRIPTION OF THE INVENTION

The invention applies to the quality control of images obtained by 2D or 3D tomographic imaging, e.g. of an aviation part made out of composite material, such as a fan blade for a gas turbine engine.

In known manner, X-ray absorption tomography is a nondestructive technique that makes it possible to reconstruct image "slices" of a three-dimensional part. Its principle relies on multidirectional analysis of the intersection between an X-ray beam and the material, by using detectors to record the radiation transmitted after passing through the part being inspected. The data acquired while taking a measurement is collected along multiple orientations. On the basis of such data, a digital image is created and mathematically reconstructed as amplitude values, each of which represents, point-by-point, the local attenuation coefficient of the material. This image, after calibration, can be converted into a density scale.

Quality control for images acquired by the tomographic imaging appliance is performed by using phantoms (also known as image quality indicators (IQI)), which are always put into place together with the part for inspection when taking measurements. The purpose of such phantoms is to measure the resolution of the images acquired by tomography by making it possible in such images to distinguish between two elements of small size but that are spaced apart from each other. Phantoms also make it possible to measure density resolution.

Figure 1:
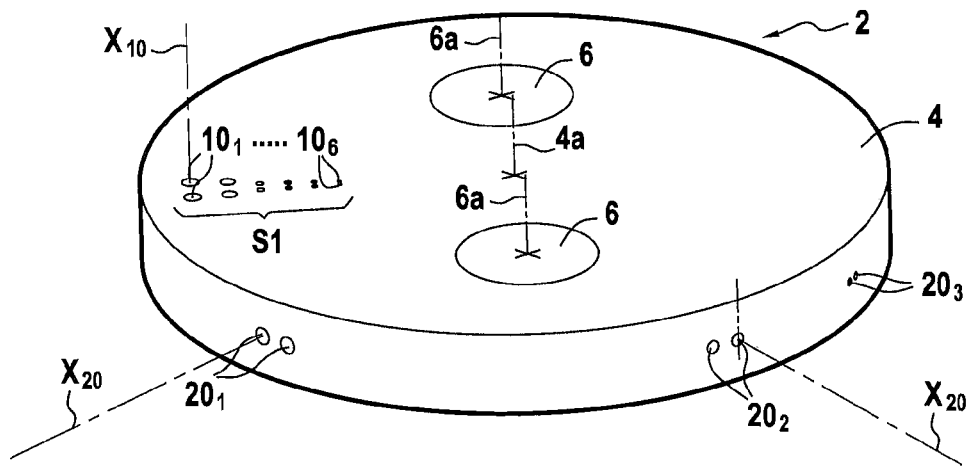
FIGS. 1 and 2 are views of a phantom of the invention, respectively shown in perspective and in a face view.
Figure 2:
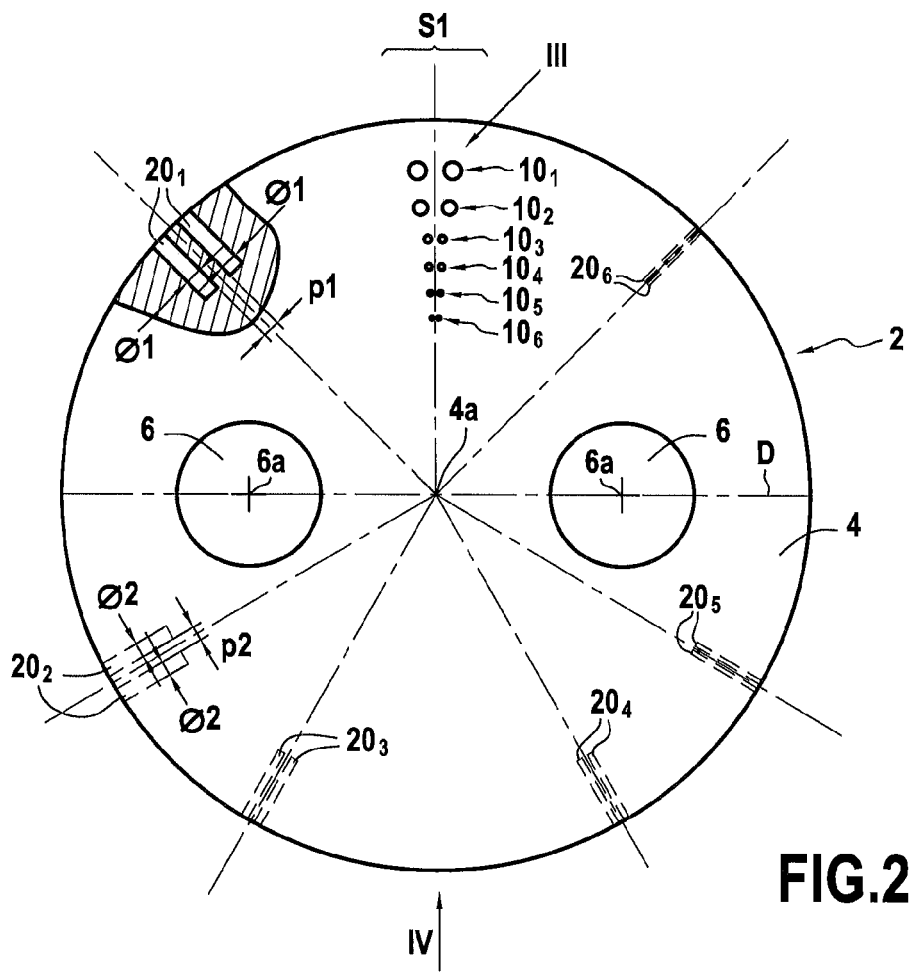
Figure 3:
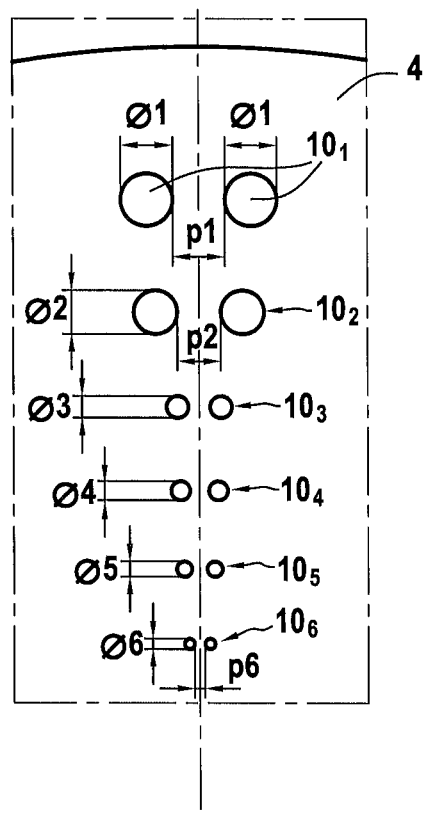
FIG. 3 is an enlargement of FIG. 2 showing a series of holes drilled in the plate of the phantom.

For this purpose, and as shown in FIGS. 1 to 3, the phantom 2 of the invention comprises in particular a cylindrical plate 4 having two cylinders 6 inserted therein and having two series S1 and S2 of hole pairs formed therein.

More precisely, the plate 4 presents an axis of revolution 4a and is made out of uniform material, for example a thermoplastic material, that is of density d1 that is close to the density of the material from which the part for inspection is made.

By way of example, in order to inspect a part made of composite material having relative density of about 1.6 (as may apply in particular to a turbojet fan blade made of composite material), the plastics material of the plate 2 should be selected to have a relative density d1 lying in the range 1.2 to 1.8.

Each of the two cylinders 6 inserted in the plate presents a respective axis of revolution 6a. These cylinders are likewise made of uniform plastic materials having respective densities d2 and d3 that are different from each other and that lie on opposite sides of the density of the composite material from which the part for inspection is made (and thus of the relative density d1 of the plate). In other words, the plastics materials of the plate 4 and of the cylinders 6 inserted therein are selected in such a manner that: d2 (or d3)<d1<d3 (or d2).

By way of example, for a composite material having a relative density of about 1.6, a plastics material having a relative density d2 of 1.1 should be selected for one of the cylinders 6, and a plastics material having a relative density d3 of 2.2 should be selected for the other cylinder. For this purpose, the plastics material used for making the cylinders may be polytetrafluoroethylene (PTFE) and a polyamide of the Nylon® type.

Thus, the phantom 2 of the invention is made of three materials having different densities, thereby making it possible to establish a calibration curve for measuring the density of the part being inspected.

As shown in FIG. 2, the respective axes of revolution 6a of the two cylinders 6 inserted in the plate are parallel to the axis of revolution 4a of said plate, and advantageously lie on a common diameter D of the plate.

Furthermore, as mentioned above, the plate 4 of the phantom of the invention also has two series S1, S2 of pairs of holes, namely a first series S1 of n pairs of holes $10_1$ to $10_n$ (six pairs of holes $10_1$ to $10_6$ in the example shown) each having an axis $X_{10}$ that is oriented axially (relative to the axis of revolution 4a of the plate), and a second series S2 of n pairs of holes $20_1$ to $20_n$ (six pairs of holes $20_1$ to $20_6$ in the example shown) each having an axis $X_{20}$ that is oriented radially (relative to the axis of revolution 4a of the plate). In the presently described example, the axis $X_{10}$ (shown in FIG. 1 for one of the holes $10_1$) corresponds to the axis along which the cylindrical holes $10_1$ to $10_6$ extend, this axis $X_{10}$ being parallel to the axis of revolution 4a of the plate 4, which is also cylindrical. Still in the presently described example, the axes $X_{20}$ (shown in FIG. 1 for one of the holes $20_1$ and for one of the holes $20_2$) correspond to the axes along which the cylindrical holes $20_1$ to $20_6$ extend, these axes $X_{20}$ being perpendicular to the axes of revolution 4a of the plate 4, which is also cylindrical, each axis $X_{20}$ possibly being parallel to a radius of the plate 4, for example.

It should be observed that for quality control of 2D tomographic imaging, only the first series S1 of the pairs of holes is necessary, whereas for quality control of 3D tomographic imaging, both series S1 and S2 of pairs of holes are necessary.

The holes in a given pair (whether of the first series S1 or of the second series S2) have the same diameter. In contrast, the different pairs of holes in a given series have different diameters.

Furthermore, the holes $20_1$ to $20_n$ of the second series S2 are spaced apart from each other in pairs by distances equal to their diameters. Thus, in the example shown in the figures, both holes $20_1$ have the same diameter Ø1 and are spaced apart from each other by a distance p1 equal to their diameter Ø1. Likewise, the holes $20_2$ have the same diameter Ø2 and they are spaced apart by a distance p2 that is equal to their diameter Ø2, etc.

Also, the depth of the holes $20_1$ to $20_n$ in the second series S2 must not be too great in order to avoid giving rise to artifacts. By way of example, a depth of about 5 mm may be selected.

In the same manner, the holes $10_1$ to $10_n$ of the first series S1 are spaced apart from each other in pairs by respective distances (p1, p2, p3, . . . , pn) equal to their diameters (Ø1, Ø2, Ø3, . . . , Øn). In the example shown, it should also be observed that the holes $20_1$ to $20_6$ of the first series S1 are of diameters identical to the holes $20_1$ to $20_6$ of the second series S2, i.e. the pair of holes $10_1$ of the first series S1 and the pair of holes $20_1$ of the second series S2 all have the same diameter Ø1, etc.

Figure 4:
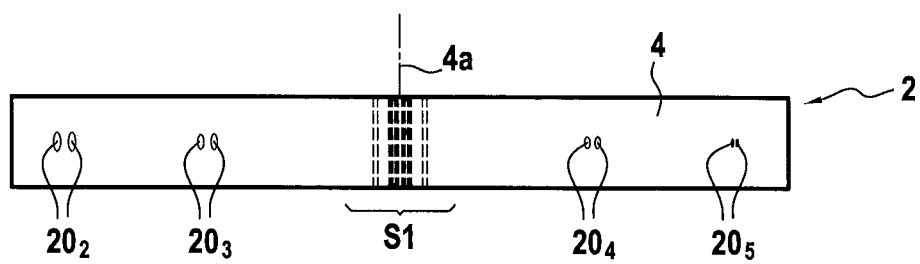
FIG. 4 is a side view of the phantom of FIGS. 1 and 2.

As shown in particular in FIGS. 2 and 4, the holes $20_1$ to $20_n$ of the second series S2 open out in the peripheral edge of the plate 4 at the same height of said peripheral edge (their respective axes are aligned on a common height of the plate taken in its thickness direction). Furthermore, these holes $20_1$ to $20_n$ of the second series S2 are angularly distributed around the axis of revolution 4a of the plate.

As for the holes $10_1$ to $10_n$ of the first series S1, they open out in two opposite faces of the plate 4 so as to pass through the plate in its thickness direction (see FIG. 4).

Furthermore, the pairs of holes $10_1$ to $10_n$ of the first series S1 are advantageously arranged on different diameters of the plate in decreasing order of diameter going from the outside of the plate towards its inside. Thus, the holes $10_1$ having the largest diameter Ø1 are arranged at the outside of the plate, and the holes $10_n$ having the smallest diameter Øn are arranged at the inside of the plate. This characteristic thus makes it possible to increase the contrast measurement range.

An example of dimensions for making a phantom for use in the context of controlling the quality of tomographic images of a turbojet fan blade made of composite material is given in the table below (where values are in millimeters).

| plate diameter | plate thickness | cylinder diameter | Ø1 p1 | Ø2 p2 | Ø3 p3 | Ø4 p4 | Ø5 p5 | Ø6 p6 |
| --- | --- | --- | --- | --- | --- | --- | --- | --- |
| 50 | 6 | 10 | 1.2 | 1.0 | 0.5 | 0.4 | 0.3 | 0.2 |

Phantoms of such dimensions are particularly advantageous for quality control of tomographic images of a turbojet fan blade made of composite material. For this purpose, two phantoms having these dimensions are always positioned together with the blade for inspection while measurements are being taken, one of the phantoms being placed under the root of the blade and the other phantom being placed offset above the tip of the blade. Tomographic imaging of the blade is then performed four times over in its height direction so that the first and the fourth tomographic images contain one of the phantoms in order to perform quality control.

The resolution (and thus the quality) of the first and fourth tomographic images is inspected by measuring between two holes in a given pair of holes (belonging to the series S1, S2): if an amplitude value difference between these two holes is observed that is greater than a preestablished value, then it is considered that the image being inspected is lacking in quality. Furthermore, if it is concluded that the first and fourth tomographic images as inspected in this way do not present any defect, it can then be considered that the two intermediate images are likewise defect free.

The invention claimed is:

1. A phantom for use in quality control of tomographic images, and comprising:
    a cylindrical plate made of a uniform material having density d1, said cylindrical plate presenting an axis of revolution;
    two cylinders inserted in the plate, the two cylinders being made of uniform material having different densities d2, d3, the density of one of the two cylinders being greater than the density d1 of the plate, and the density of the other cylinder being less than the density d1 of the plate; and
    a first series of pairs of holes of different diameters drilled in the plate, the holes of the first series extending along axes that are parallel to the axis of revolution of the plate, and
    a second series of pairs of holes of different diameters drilled in the plate, the holes of the second series extending along axes perpendicular to the axis of revolution of the plate so that said holes of the second series extend radially in the cylindrical plate.

2. A phantom according to claim 1, wherein the holes in any given pair of holes of the first series or of the second series of pairs of holes are spaced apart from each other by a distance equal to their diameter.

3. A phantom according to claim 2, wherein the holes of the first series are of diameters that are identical to the holes of the second series.

4. A phantom according to claim 1, wherein the holes of the second series open out into a peripheral edge of the plate at the same height of said peripheral edge.

5. A phantom according to claim 4, wherein the holes of the second series are angularly distributed around the axis of revolution of the plate.

6. A phantom according to claim 1, wherein the holes of the first series open out into two opposite faces of the plate, the pairs of holes being arranged on different diameters of the plate.

7. A phantom according to claim 6, wherein the pairs of holes of the first series are arranged in order of decreasing diameter between the outer periphery of the plate and the center of said plate.

8. A phantom according to claim 1, wherein the plate is made of a uniform material having a relative density d1 lying in the range 1.2 to 8.

9. A phantom according to claim 1, wherein the two cylinders inserted in the plate have respective axes of revolution that are positioned on a common diameter of the plate.

10. A method comprising utilizing at least one phantom according to claim 1, for quality control in tomographic imaging of a gas turbine engine fan blade made out of composite material, wherein the plate presents a diameter of about 50 mm and a thickness of about 6 mm, each of the two cylinders has a diameter of about 10 mm, and the holes of the first series of holes have diameters lying in the range 0.2 mm to 1.2 mm, approximately.

* * * * *